US00PP31453P2

(12) United States Plant Patent
Hansen

(10) Patent No.: US PP31,453 P2
(45) Date of Patent: Feb. 18, 2020

(54) *DIANTHUS* PLANT NAMED 'CUTE AS A BUTTON'

(50) Latin Name: *Dianthus hybrid*
Varietal Denomination: Cute as a Button

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,940

(22) Filed: Feb. 1, 2019

(51) Int. Cl.
*A01H 5/02* (2018.01)
*A01H 6/30* (2018.01)

(52) U.S. Cl.
USPC ..... Plt./276

(58) Field of Classification Search
USPC ..... Plt./272, 273, 276, 277
See application file for complete search history.

*Primary Examiner* — Susan McCormick Ewoldt

(57) ABSTRACT

A new and unique plant cultivar of perennial carnation or pinks, *Dianthus* plant named 'Cute as a Button' with numerous, medium-sized, semi-double, lightly-fragrant flowers producing a rounded flat face. The numerous stems cover top to bottom of clump on well-branched stems having up to 3 flowers per stem. Petals are bright pink maturing medium pink and have fine serrations. The habit is compact with long, thin, blue-green foliage.

1 Drawing Sheet

Botanical denomination: *Dianthus* hybrid.
Cultivar designation: 'Cute as a Button'.

STATEMENT REGARDING PRIOR DISCLOSURES UNDER 37 CFR 1.77(b)(6)

The first public disclosure of the claimed plant, in the form of a website to the public and email release to customers, was made by Walters Gardens, Inc. on Feb. 1, 2018. The first sales of the claimed plant was on Jul. 9, 2018 by Walters Gardens, Inc. Walters Gardens, Inc. obtained the new plant and information about the new plant directly from the inventor. No plants of *Dianthus* 'Cute as a Button' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of carnation or pinks from the genus *Dianthus* and given the cultivar name 'Cute as a Button'. The new plant was the result of an intentional cross on Jun. 23, 2013 under the direction of the inventor between the unnamed, proprietary hybrid known by the breeder code 11-167-01 as the female or seed parent and the unnamed, proprietary hybrid known by the breeder code 11-283-1 as the male or pollen parent. The cross was harvested and sown in the summer of 2013. The new hybrid was first selected from trials at a wholesale perennial nursery in Zeeland, Mich. during the summer of 2015 as a single seedling clone and given the breeder code number 13-50-2 later in the evaluation processes. *Dianthus* 'Cute as a Button' has been asexually propagated at the same nursery in Zeeland, Mich. since 2013 using traditional shoot tip cutting procedures and later sterile shoot-tip tissue culture and found to reproduce plants that are identical and exhibit all the characteristics of the original plant.

SUMMARY OF THE INVENTION

*Dianthus* 'Cute as a Button' has not been evaluated under all possible environmental conditions. The phenotype may vary with variations in environment including: growing temperature, available sunlight, nutrients, water, etc. without a change in the genotype of the plant.

Plants nor photographs of the two parent were not maintained so comparison is not possible. The new plant can be compared with the grandparents: 'Pomegranate Kiss' U.S. Plant Pat. No. 21,895, 'Devon Flavia' U.S. Plant Pat. No. 15,903 and 'Devon Xera' U.S. Plant Pat. No. 14,895. 'Pomegranate Kiss' has 16 to 22 petals per flower of a different hue of purplish-red. 'Devon Flavia' has pink and reddish-purple flowers with 19 to 20 petals per plant. 'Devon Xera' has crimson-colored single flowers from May through September. The nearest comparison cultivars known to the inventor are: 'Electric Red' U.S. Plant Pat. No. 29,591, 'Stardust' U.S. Plant Pat. No. 20,999 and copending application Ser. No. 16/350,942 'Appleblossom Burst'. 'Electric Red' has a solid, bright red colored flower. 'Stardust' has flowers that are coral pink in color. 'Appleblossom Burst' has a greater color change in the flowers becoming near white to pale pink and denser in habit.

*Dianthus* 'Cute as a Button' is distinct from its parents and all other *Dianthus* known to the applicant in the following combined traits:

1. Semi-double flowers opening up with a full flat face.
2. Petals open a bright pink with darker red bar near the base of the petal limb.
3. Petal color lightens with age to a medium pink;
4. Petal margin irregularly toothed;
5. Multiple flowers per stiff, upright peduncle;

6. Medium flower size producing a lightly-sweet spicy fragrance;
7. Compact habit and dense blue-green foliage.

BRIEF DESCRIPTION OF THE DRAWINGS

The photographs of 'Cute as a Button' are of a two-year-old plant grown in full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
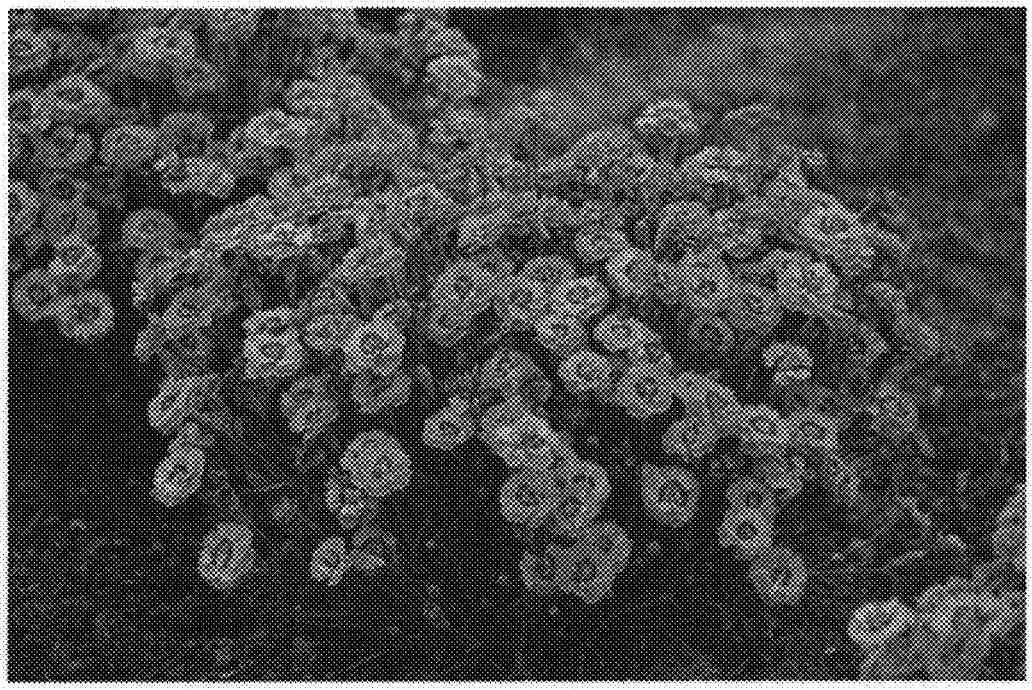
FIG. 1 shows the habit of the plant in mid-season flowering.
Figure 2:
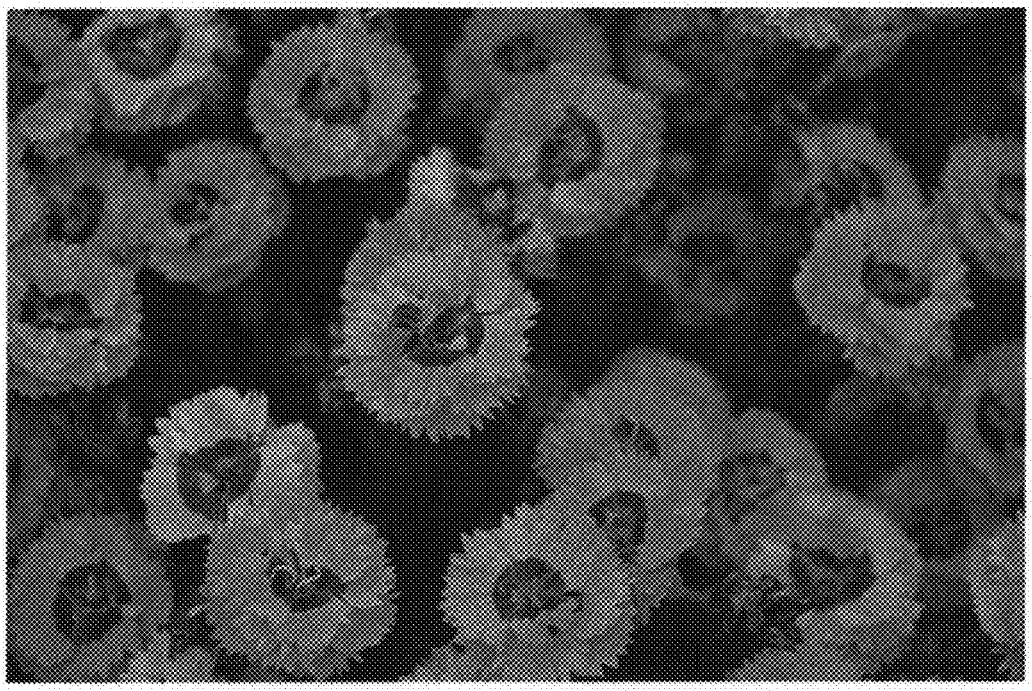
FIG. 2 shows a close-up of the flowers and bud.

The following detailed description of the new plant is based on observations of two-year-old plants in a partially shaded greenhouse and also full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 11-167-01; the male or pollen parent is 11-283-1;

Plant habit: Caespitose, herbaceous, evergreen, winter-hardy perennial; stems and peduncles highly branched, mostly erect stems; height of foliage about 15.0 cm and about 48.0 cm across; height in flower is about 18.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous both adaxial and abaxial; margin entire to microscopically serrulate; acute narrowly apex; base truncate, decurrent, clasping; no fragrance detected.

*Leaf dimensions*.—To about 6.7 cm long and about 2.5 mm wide, average about 6.0 cm long and 2.2 mm wide.

*Leaf color*.—Young expanding leaves adaxial and abaxial blend between RHS N137D and RHS 189B; mature abaxial adaxial blend between RHS N137D and RHS 189B.

*Venation*.—Not pronounced; obscurely pinnate, coloration same as that of leaf top and bottom.

Stems: About 60 per plant; upright; cylindrical, glabrous, glaucous; solid; branching in upper nodes;

*Stem size*.—About 12.0 cm long to peduncle and about 3.0 mm wide at base.

*Stem color*.—Blend between RHS N138D and RHS 122A.

*Branching*.—Numerous; typically alternate from upper nodes; about 5 per main stem and about 200 per plant; branch size average about 3.5 cm long and 1.0 mm diameter at time of initial flowering.

*Nodes*.—About 3.5 mm across; color nearest RHS 142D.

*Internodes*.—About 12 per stem before peduncle; average about 1.9 cm apart depending on growing temperature, shorter in cooler conditions.

Inflorescence:

*Type*.—Terminal, cymose; perfect; salverform; actinomophic; semi-double.

*Attitude*.—Upright to slightly outward around perimeter of plant.

*Dimension*.—About 3.4 cm across and extending about 3.0 cm above base of calyx tube and 7.0 mm wide at apex of calyx.

*Flowers per stem*.—Up to 3, average 2.

*Pedicel*.—Glaucous, glabrous, cylindrical, stiff; primarily upright.

*Pedicel size*.—Terminal flower to about 3.4 mm long and about 1.5 mm diameter; other flowers average about 2.0 mm long and 1.0 mm diameter.

*Pedicel color*.—Nearest blend between RHS 122D and RHS 189B.

*Flower bud*.—Slowly opening; glabrous; glaucous; with calyx still closed: ellipsoid with rounded base and acute apex; about 18.0 mm long and 6.0 mm across at distal fusion point of sepals; with petals extended beyond calyx and still parallel to calyx side: terete, with rounded base and truncate apex or petal tops, about 25.0 mm long and 10.0 mm across near apices of petals.

*Flower bud color*.—With petals enclosed in calyx distally variable with striations of nearest RHS 146C and RHS 141B in basal portion and distally nearest blend of RHS 189D and RHS 122D; with petals extended beyond calyx petal portion nearest RHS 71A.

*Flower period*.—Beginning late spring and continuing for about three weeks.

*Flower fragrance*.—Light, sweet spicy, clove-like.

*Flower lasting quality*.—Individually about seven to ten days on or cut from plant.

*Petals*.—Glabrous; up to about 16 per flower, average about 15; consisting of a rounded blade or limb and a claw; limb and claw combined are flabellate; limb apex and margin with fine irregular dentations average 2.0 mm wide and 1.5 mm long; limb bent outwardly in distal 15.0 mm to nearly a ninety degree angle creating a flat rounded face; persistent.

*Petal dimensions*.—Limb to about 19.0 mm across, average about 17.0 mm across; claw tapering to attenuate base of about 1.0 mm across; whole petal to about 30.0 mm long, average about 28.5 mm long.

*Petal color*.—Young abaxial claw nearest RHS 145D, young abaxial limb center lighter than RHS 72D; young adaxial claw nearest RHS 145D, young adaxial limb between RHS 71C and RHS 71D with 3.0 mm long bar stretching at base of limb between RHS 71A and RHS 187C; mature abaxial claw nearest RHS 145D, mature abaxial limb between RHS 77C and RHS 77D; mature adaxial claw nearest RHS 145D, mature adaxial limb between RHS N74C and RHS N74D with said bar nearest RHS 71A and distal limb nearest RHS N74C.

*Calyx*.—Terete to campanulate; to about 18.0 mm long and 7.0 mm diameter at apex.

*Sepals*.—Five; acute apex and fused in basal 13.0 mm forming five-toothed calyx tube; glabrous; glaucous abaxial; margins entire to micro-ciliolate.

*Sepal size*.—Individually about 18.0 mm long and about 3.0 mm across at distal fusion.

*Sepal color*.—Abaxial margin translucent to nearest RHS 157C, mid-portion nearest RHS 137A with heavy glaucous covering nearest RHS 189C, base nearest RHS 146D; adaxial margin translucent to nearest RHS 157C, mid-portion nearest RHS 147C, base nearest RHS 147D.

*Peduncle*.—Glabrous; glaucous; solid, cylindrical; stiff; about 8.0 cm long and about 2.5 mm diameter at base; attitude mostly upright.

*Peduncle color*.—Blend between RHS 122A and RHS 189B with glaucous bloom, nearest RHS 137A without glaucous bloom.

*Epicalyx*.—Two pairs subtending each flower; opposite, glaucous, glabrous; sessile, margin entire, broadly lanceolate to deltoid; inner pair with broadly acute apex and truncate base; outer pair with acuminate apex truncate base; and outer pair about 8.5 mm long and about 4.0 mm wide; inner pair about 8.0 mm long and about 8.0 mm across near middle.

*Epicalyx color*.—Both pairs abaxial variable mottled with apex nearest RHS 137A, margin translucent to nearest RHS 155C and center mixture of RHS 137A and RHS 160C; adaxial apex nearest RHS 137A, center and base nearest RHS 137D, margin translucent to nearest RHS 160D.

*Androecium*.—Nine to ten; not fully developed; applanate along ovary; to about 8.0 mm long; Filaments: to about 6.5 mm long and 0.5 mm diameter; color nearest RHS NN155D; Anther: auriculate; acute apex and auriculate base; basifixed; about 1.5 mm long and 1.0 mm wide and 0.2 mm thick; not fully developed; color between RHS 165B and RHS 165C; Pollen: not observed.

*Gynoecium*.—Single; to about 27.0 mm long; Style: bifurcate just above ovary; to 5.0 mm long; color nearest RHS NN155D; Stigma: slightly flattened abaxial to adaxial; puberulent; about 15.0 mm long and 1.0 mm wide; color nearest RHS N155D; Ovary: superior; ellipsoid-shaped with broadly acute apex and truncate base; about 5.0 mm long and 5.5 mm wide; color between RHS 150D and RHS 145D.

Fruit: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Cute as a Button' essentially as herein described and illustrated.

* * * * *